United States Patent [19]

Rosenberg

[11] 4,107,331

[45] Aug. 15, 1978

[54] ZINC CHELATING FUNGICIDAL COMPOSITION

[76] Inventor: Max Rosenberg, 1721 Nashville Ave., New Orleans, La. 70115

[21] Appl. No.: 664,361

[22] Filed: Mar. 5, 1976

[51] Int. Cl.$^2$ .......................... A01N 9/20; A01N 9/22
[52] U.S. Cl. ..................................... 424/319; 424/263
[58] Field of Search ......................................... 424/319

[56] References Cited

U.S. PATENT DOCUMENTS

| 2,836,537 | 5/1958 | Skaptason | 424/319 X |
| 2,875,129 | 2/1959 | Bersworth et al. | 424/319 |
| 3,052,604 | 9/1962 | Davis et al. | 424/319 |
| 3,184,381 | 5/1965 | Ashmead et al. | 424/319 X |
| 3,240,701 | 3/1966 | Furia | 424/319 X |
| 3,514,481 | 5/1970 | Gordon | 260/519 |
| 3,935,862 | 2/1976 | Kraskin | 128/287 |
| 3,950,536 | 4/1976 | Barer et al. | 424/319 |

OTHER PUBLICATIONS

Weinberg, "Infectious Diseases Influenced by Trace Element Environment", Annal. of the New York Academy of Sciences, vol. 199, pp. 274–282. 6/72.
Goodman et al., The Pharmacological Basis of Therapeutics, 3rd Ed., pp. 934–935.
Halsted et al., The Lancet, 2/70, pp. 322–324.

*Primary Examiner*—Allen J. Robinson
*Attorney, Agent, or Firm*—Cushman, Darby & Cushman

[57] ABSTRACT

Fungi requiring zinc ions are killed by applying to the fungi compounds capable of chelating zinc in concentrations of at least 3.5%. The invention is particularly effective in treating candida albicans.

22 Claims, No Drawings

ZINC CHELATING FUNGICIDAL COMPOSITION

The present invention relates to the treatment of fungal disease of man and other mammals caused by fungi, such as candida albicans, cryptococcus neoformans, tarulopsis, candida tropicalis, penicillium and other fungi pathogenic to human beings.

It is known that fungi require zinc ions to carry out the process of secondary metabolism necessary for their growth, Eugene D. Weinberg, "Infectious diseases influenced by trace element environment", Annal of the New York Academy of Sciences, Vol. 199, p. 274–284, June 28, 1972.

It has now been discovered that the application of the water soluble salts of ethylenediaminetetracetic acid (EDTA) to growths of fungi or to tissue infected with fungi results in control of fungal growth. While all non-toxic water soluble forms of the chelating agents have fungistatic properties when applied in the proper concentration, the preferred cation form of the chelating agent for use in human beings is the calcium cation complex. It has been found the EDTA salts exert good fungistatic activity in the 5 to 10% range and higher, although limitation of concentration should be governed by the sensitivity of tissue to higher concentrations. Specific chelating agents which have stability constants (an indicator of the strength of metal binding) higher than that of ethylenediaminetetracetic acid, such as diethylenetriaminepentaacetic acid and 1,2 diaminocyclohexane-N,N'tetraacetic acid, also show good fungistatic activity around the level of 2% concentration or above. The anti-fungal agent should have a stability constant for zinc ion in the range of 14.5 to 18.7. "Stability constant" expresses the tenacity of the particular bond made in the metal complex between the sequestering agent and the metal ion. It is derived from certain laboratory data and is calculated from a mathematical formula, see S. Chaberek and A. D. Martell "Organic Sequestering Agents," New York, Wiley, 1959, which has a table which contains an extensive list of sequestering agents and their stability constants for various metals, including zinc. The chelating agents specifically mentioned in the present specification are listed in Chaberek and have stability constants ranging from 14.5 to 18.7. The chelating ability of the sequestering agent is increased by maintaining an alkaline pH in the range of 7 to 10. However, acid pH ranges can also be used, e.g., a pH of 4.5 and up to 7. Suitable chelating agents in addition to those set forth above are ethylene bis N,N'-(2-aminomethyl)-pyridine-N,N'-diacetic acid, B-mercaptoethylimino-diacetic acid, tetrakis (2-aminoethyl)-ethylenediamine, B,B',B"-triaminotriethylamine, N-hydroxyethylethylenediaminetriacetic acid, ethylenediamine N,N-dipropionic acid, N,N'-diacetic acid and aminocarboxylic acids having a stability constant of 14.5 or above for zinc ion.

The compounds are normally used in the form of their non-toxic salts, e.g., alkali and alkaline earth metal salts, such as the sodium, potassium or calcium salts. Mixed salts can also be used. Thus the presently preferred salt is the calcium disodium salt of EDTA. This salt is also known as calcium disodium edetate.

Calcium disodium edetate is available in three proprietary pharmaceutical preparations, Boyle Company of Los Angeles:

(a) Triva powder: Each dose contains 0.33% of calcium disodium edetate in 3 grams of powder to be diluted with one quart of water for use,
(b) Triva Jel: 2.5 mg of calcium disodium edetate is present in the 5000 mg dose of applied jelly.

Schmidt Laboratories of Little Falls, N.J.:

(a) Vagisec liquid: The quantity of calcium disodium edetate is not listed in the Physicians Desk Reference (PDR) but each dose is 5 cc of liquid which is to be diluted in one quart of water,
(b) Vagisec plus suppositories: Each dose contains 0.022% of calcium disodium edetate in a 3000 mg suppository. Reed and Carnrick of Kenilworth, N.J.:

Trichotine liquid vaginal cleanser: The quantity of calcium disodium edetate is unlisted in the P.D.R. Each dose dilution is 2 capfuls in one quart of water. None of these prescription drugs as published in the Physicians Desk Reference claim any antifungal effect for the calcium disodium edetate. In addition, these therapeutic preparations contain such extremely minute amounts of the calcium disodium edetate that no antifungal activity could be detected.

The Riker Laboratories also sell a calcium disodium edetate solution, 20% concentration for intravenous infusion, subcutaneously or intramuscular injection to reduce the blood levels in lead poisoning and lead encephalopathy and indicates it might be useful in chelation of radioactive and nuclear fission products as well as in the treatment of poisoning from other heavy metals having a greater affinity for the chelating agent than does calcium. In intravenous administration 5 ml of the solution is diluted with 250–500 ml of isotonic sodium chloride or 5% dextrose solution in water. There is no indication of or claim for antifungal activity.

Davis U.S. Pat. No. 3,052,604 shows that the combination of tetrasodium edetate and certain polyoxyethylene alkyl phenols are effective bactericides using a concentration of about 5.5% of the edetate. Davis does not show the use of sodium edetate alone. Applicant has been unable to find any antibacterial activity exhibited in his tests with calcium disodium edetate.

Thus the ability to employ the chelating agents at a concentration of at least 5% to treat infections caused by fungi which require zinc ions in carrying the process of secondary metabolism necessary for their growth is unexpected.

It is particularly surprising that the chelating agents are effective in treating vaginal infections caused by fungi such as candida albicans.

The chelating agent is normally applied together with an inert non-toxic carrier which can comprise or consist of water, for example. Such carriers include, for example, in addition to water, aqueous jelly, gelatin capsules, water soluble creams, enteric coated tablets, e.g., cellulose acetate-phthalate coated tablets.

The chelating is preferably employed having a concentration of 5 to 10%. However, higher concentrations, e.g., 20% or even up to 100% are also antifungal. For clinical effectiveness at least 5% of the chelating agent is preferred although lesser concentrations, e.g., as low as 3.5% show some antifungal activity.

Unless otherwise indicated, all parts and percentages are by weight.

EXAMPLES

1. IN VITRO STUDIES

The effect of chelating agents upon the growth of the various pathogenic fungi set forth above was determined by disc sensitivity studies using the method of Kirby-Bauer wherein varying concentrations of chelating agents in their aqueous form were applied to Sabouraud's agar inoculated with fungi. Zones of fungal growth inhibition were shown to be significant where the chelating agent concentration was used in the 5 to 10% and above range, e.g., 20%. The degree of inhibition of fungal growth also was found to be in direct relation to the stability constant of the chelating agent, with a higher stability constant resulting in larger zones of growth inhibition. Thus specific tests were carried out at 5% and 10%. The results were read at 24 and 48 hours. The findings showed that the zone of inhibition ranged from 18 mm to over 35 mm, the size varying with the concentration of the reagent.

Other studies demonstrated that the addition of a small excess of zinc ion (as $ZnSO_4$) resulted in the neutralization of the fungistatic effect of the chelating agent. The result of this particular study is consistent with the explanation of the role that zinc ion plays in the interaction between chelating agents and fungal growth.

2. IN VIVO STUDIES

Clinical studies, utilizing 5% and 6% concentrations of ethylenediaminetetraacetic acid (as calcium disodium edetate) in an aqueous jelly (K-Y jelly) as a vehicle, were undertaken to determine the clinical effectiveness of the chelating agent as treatment for vaginal candida albicans infections. Over 90% cure was attained as proven by post treatment Nickerson cultures for candida.

More specifically in determining the effect of EDTA upon vaginal candidiasis using calcium disodium edetate as the EDTA source, a pilot clinical study was undertaken which included 45 gynecologic patients. All cases were diagnosed as having vaginal candidiasis by positive Nickerson media cultures prior to institution of treatment. Each patient was given a two ounce tube of chelating agent-jelly and a vaginal applicator. The patient instilled 4 to 5 cc of jelly intravaginally for eight to ten nights, at bedtime. Two to four weeks after therapy was completed, the patients had repeat Nickerson's cultures. Of the 45 patients treated with the chelating agent jelly, 40 patients had negative Nickerson's cultures giving an 88% cure rate with first treatment. This 88% figure increased to more than 90% when the successful retreatment cases are added. The chelating agent-jelly was prepared by adding calcium disodium edetate in sufficient quantity to the jelly to produce a 5% concentration. The jelly vehicle was the water soluble "K-Y" jelly containing sodium carboxy methyl cellulose as the major ingredient.

A lesser number of patients were tested using 6% concentration of the calcium disodium edetate and from the results obtained, it appeared that the jelly having 6% of the EDTA salt was equally effective to that containing 5% of the salt.

The clinical application of the fungistatic effect of chelating agents can be extended to other organ systems by modifying the delivery vehicle. For example:

(1) They can be used to treat fungal disease of the skin by applying them to the skin as a water soluble cream, lotion, or as a talc-like dusting powder, both in the appropriate concentrations and adjusted to an alkaline pH, i.e., 7–10.

(2) They may be used to treat candida overgrowth in the large bowel by oral administration of enteric coated tablets.

(3) They may be prepared as a vaginal douche solution in the proper concentration, e.g., 5%, and at the optimum alkaline pH, e.g., 8 as part of a system of vaginal candida control.

(4) Using the appropriate concentration, e.g., 6% of the chelating agent at an alkaline pH, e.g., 8.5, water soluble vaginal suppositories can be prepared for vaginal candida infection.

While the invention is primarily concerned with treating fungal infections of man, it can also be used in treating fungal infections of other mammals commonly infected with fungal infections such as mice, dogs, cats, horses, cattle and sheep, for example.

The compositions employed can comprise, consist essentially of or consist of the materials set forth.

What is claimed is:

1. A process of killing fungi requiring zinc ions to carry out the process of secondary metabolism necessary for their growth comprising administering to a mammal having an infection caused by such fungi a compound capable of chelating zinc ions in a concentration of at least 3.5% and a pH of about 4.5 to 10 in an amount effective to control said fungi, said compound being selected from the group consisting of non-toxic water soluble salts of ethylenediaminetetraacetic acid, diethylenetriaminepentaacetic acid, 1,2-diaminocyclohexane-N,N'-tetraacetic acid, β-mercaptoethyliminodiacetic acid, tetrakis (2-aminoethyl)-ethylenediamine, B,B',B"-triaminotriethylamine, N-hydroxyethylethylenediaminetriacetic acid and ethylenediamine N,N-dipropionic acid N,N'-diacetic acid.

2. The process according to claim 1 wherein the chelating agent is selected from the group consisting of non-toxic water soluble salt of ethylenediamine-tetraacetic acid, diethylenetriaminepentaacetic acid, 1,2-diaminocyclohexane-N,N'-tetraacetic acid.

3. The process according to claim 1 wherein the chelate is administered orally, topically or vaginally and at a concentration of at least 5%.

4. The process according to claim 1 wherein the chelating agent is a calcium salt.

5. The process according to claim 1 wherein the chelating agent is a non-toxic water soluble salt of ethylenediamine-tetraacetic acid.

6. The process according to claim 5 wherein the chelating agent is a calcium salt.

7. The process according to claim 6 wherein the salt is calcium disodium edetate.

8. The process according to claim 7 wherein the pH is 7 to 14.

9. The process according to claim 1 wherein the concentration is 5 to 20%.

10. The process according to claim 9 wherein the concentration is 5 to 10%.

11. The process according to claim 1 wherein the chelating agent is administered to the vagina to control a fungal infection thereof.

12. The process according to claim 11 wherein the chelating agent is a water soluble non-toxic salt of ethylenediaminetetraacetic acid.

13. The process according to claim 12 wherein the chelating agent is calcium disodium edetate.

14. The process according to claim 13 wherein the fungal infection is an infection caused by candida albicans.

15. The process according to claim 14 wherein the chelating agent is applied as a 5% aqueous jelly.

16. The process according to claim 14 wherein the chelating agent is applied as a 6% aqueous jelly.

17. The process according to claim 14 wherein the chelating agent is applied as a 5-10% vaginal douche solution.

18. The process according to claim 14 wherein the chelating agent is applied as a water soluble suppository containing 5-10% of the chelating agent.

19. The process according to claim 14 wherein the chelating agent is administered to the vagina to control a fungal infection thereof.

20. The process according to claim 11 wherein the fungal infection is caused by candida albicans.

21. The process according to claim 20 wherein the composition administered consists essentially of the chelating agent and an inert non-toxic carrier.

22. The process according to claim 1 wherein the pH is 7 to 10.

* * * * *